(12) United States Patent
Adler et al.

(10) Patent No.: US 8,460,884 B2
(45) Date of Patent: Jun. 11, 2013

(54) USE OF HEMATOPOIETIC GROWTH FACTOR INDUCIBLE NEUROKININ-1 (HGFIN) AS A BIOMARKER FOR RENAL INJURY OR RENAL DISEASE

(75) Inventors: Sharon Adler, Los Angeles, CA (US); Tiane Dai, Torrance, CA (US); Ying Wang, Torrance, CA (US); Mukti Patel-Chamberlin, Torrance, CA (US); Cynthia C. Nast, Rancho Palos Verdes, CA (US); Janine LaPage, Redondo Beach, CA (US); Nosratolah Dabir Vaziri, Newport Beach, CA (US); Madeleine V. Pahl, Orange, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 543 days.

(21) Appl. No.: 12/613,385

(22) Filed: Nov. 5, 2009

(65) Prior Publication Data
US 2010/0173340 A1 Jul. 8, 2010

Related U.S. Application Data

(60) Provisional application No. 61/111,690, filed on Nov. 5, 2008, provisional application No. 61/157,762, filed on Mar. 5, 2009.

(51) Int. Cl.
*G01N 33/53* (2006.01)
(52) U.S. Cl.
USPC .................. 435/7.1; 435/7.8; 435/7.9
(58) Field of Classification Search
None
See application file for complete search history.

(56) References Cited

U.S. PATENT DOCUMENTS
7,426,441 B2   9/2008   Mendrick et al.

FOREIGN PATENT DOCUMENTS
WO   WO 2006/071441   7/2006
WO   WO 2008/133641   11/2008

OTHER PUBLICATIONS

Horcajada J. P. et al., Evaluation of Inflammatory and Renal-Injury Markers in Women Treated with Antibiotics for Acute Pyelonephritis Caused by *Escherichia coli*, Clinical and Diagnostic Laboratory Immunology, Jan. 2004, vol. 11, No. 1, pp. 142-146.*
Abirami K. et al., Clinical Medicine—Urinalysis in Clinical Practice (Akin to Liquid Kidney Biopsy), Journal, Indian Academy of Clinical Medicine, Jan.-Jun. 2001, vol. 2, No. 1 and 2, pp. 39-50.*
Cheruvanky A. et al., Rapid isolation of urinary exosomal biomarkers using a nanomembrane ultrafiltration concentrator, Am. J. Physiol. Renal Physiol., May 2007, vol. 292, pp. F1657-F1661.*
Li et al. (2010) "The melanoma-associated transmembrane glycoprotein Gpnmb controls trafficking of cellular debris for degradation and is essential for tissue repair" *The FASEB Journal* 24: 1-15.
Nakamura et al. (2007) "Early induction of osteoactivin expression in rat renal tubular epithelial cells after unilateral ureteral obstruction" *Exp Toxicol Pathol* 59(1): 53-59.
Pahl et al. (2009) "Upregulation of Monocyte/Macrophage HGFIN (Gpnmb/Osteoactivin) Expression in End-Stage Renal Disease" *Clin J Am Soc Nephrol* 5: 56-61 Published online before print Oct. 2009.
Wang et al. (2008) "Hematopoietic growth factor inducible neurokinin-1 (HGFIN): Marker of injury in diverse renal disease across species." *ASN Renal Week 2008*: Abstract# 552168 pp. 1-2.
Gonzales et al. (2012) *Urinary Exosome Protein Database*. pp. 1-57 [retrieved on Oct. 21, 2012]. Retrieved from the Internet: http://dir.nhlbi.nih.gov/papers/lkem/exosome/.
Patel-Chamberlin et al. (2011) "Hematopoietic growth factor inducible neurokinin-1 (Gpnmb/Osteoactivin) is a biomarker of progressive renal injury across species" *Kidney International* 79: 1138-1148.

* cited by examiner

*Primary Examiner* — Jon P Weber
*Assistant Examiner* — Satyendra Singh
(74) *Attorney, Agent, or Firm* — Jennifer L. Wahlsten; Emily M. Haliday; Weaver Austin Villeneuve & Sampson LLP

(57) ABSTRACT

The invention provides, in certain embodiments, a method of detecting an indicator of renal injury or renal disease. The method entails assaying a urine sample for hematopoietic growth factor inducible neurokinin-1 (HGFIN), wherein the presence of HGFIN at an elevated level indicates the presence and/or degree of renal injury or renal disease, and/or the rate of loss of renal function. In other embodiments, the invention provides a method of detecting an indicator of systemic inflammation. This method entails assaying a biological sample for HGFIN, wherein the presence of HGFIN at an elevated level indicates the presence and/or degree of systemic inflammation. Also provided, are methods of determining progression of these conditions, as well as methods of determining subjects' response to treatment.

29 Claims, No Drawings

USE OF HEMATOPOIETIC GROWTH FACTOR INDUCIBLE NEUROKININ-1 (HGFIN) AS A BIOMARKER FOR RENAL INJURY OR RENAL DISEASE

CROSS-REFERENCE TO RELATED APPLICATIONS

This application claims priority to and benefit of U.S. Ser. No. 61/111,690, filed on Nov. 5, 2008, and of U.S. Ser. No. 61/157,762, filed Mar. 5, 2009, as provided for under 35 U.S.C. §119 and/or 35 U.S.C. §120, as appropriate. U.S. Ser. No. 61/111,690 and U.S. Ser. No. 61/157,762 are incorporated herein by reference, in their entireties, for all purposes.

STATEMENT AS TO RIGHTS TO INVENTIONS MADE UNDER FEDERALLY SPONSORED RESEARCH AND DEVELOPMENT

Not applicable

FIELD OF THE INVENTION

The invention relates to the use of hematopoietic growth factor inducible neurokinin-1 (HGFIN) as a marker for kidney injury, kidney disease, and/or inflammation.

SUMMARY OF THE INVENTION

The invention provides, in certain embodiments, a method of detecting an indicator of renal injury or renal disease. The method entails assaying a urine sample for hematopoietic growth factor inducible neurokinin-1 (HGFIN), wherein the presence of HGFIN at an elevated level indicates the presence and/or degree of renal injury and/or renal disease. The method can be performed, e.g., on a human urine sample. In particular embodiments, the sample is obtained from a human patient known to have, or suspected of having, renal injury or renal disease, e.g., acute renal disease or chronic renal disease. The urine sample includes, in specific embodiments, centrifuged urine and/or urinary exosomes.

In other embodiments, the invention provides a method of detecting an indicator of a subject's response to treatment for renal injury or renal disease. The method entails assaying a urine sample obtained from a subject after initiation of treatment for renal injury or renal disease for HGFIN, wherein the level of HGFIN is positively correlated with the degree of renal injury or renal disease or the rate of loss of renal function. In variations of these embodiments, a baseline level of HGFIN is measured prior to initiation of treatment for renal injury or renal disease. The HGFIN level of the urine sample after initiation of treatment can then (but need not) be compared to the baseline level of HGFIN. A decrease in the HGFIN level of the urine sample after initiation of treatment, as compared to the baseline level of HGFIN, indicates that the subject is responding to the treatment. In certain embodiments, one or more additional assays of HGFIN are performed as treatment is continued.

The methods described herein can, optionally, include the detection of one or more additional indicators of renal injury or disease, such as serum creatinine, serum cystatin-C, urine protein, urine albumin, urine N-acetyl-beta-D-glucosaminidase, urine NGAL, and urine KIM1. HGFIN and/or an additional indicator of renal injury or disease can be detected, e.g., by an immunoassay, HPLC, or mass spectroscopy.

The invention provides, in certain embodiments, a method of detecting an indicator of systemic inflammation. The method entails assaying a biological sample for HGFIN, wherein the presence of HGFIN at an elevated level indicates the presence and/or degree of systemic inflammation. The method can be performed, e.g., on a blood sample. In particular embodiments, the sample is obtained from a human, e.g., a patient known to have, or suspected of having, an inflammatory disease. The blood sample includes, in specific embodiments, monocytes and/or macrophages.

In other embodiments, the invention provides a method of detecting an indicator of a subject's response to treatment for an inflammatory disease. The method entails assaying a biological sample obtained from a subject after initiation of treatment for inflammatory disease for HGFIN, wherein the level of HGFIN is positively correlated with the degree of inflammatory disease. The method can be performed, e.g., on a blood sample. In particular embodiments, the sample is obtained from a human, e.g., a patient known to have, or suspected of having, an inflammatory disease. The blood sample includes, in specific embodiments, monocytes and/or macrophages. In variations of these embodiments, a baseline level of HGFIN is measured prior to initiation of treatment for inflammatory disease. The HGFIN level of the urine sample after initiation of treatment can then (but need not) be compared to the baseline level of HGFIN. A decrease in the HGFIN level of the biological sample after initiation of treatment, as compared to the baseline level of HGFIN, indicates that the subject is responding to the treatment. In certain embodiments, one or more additional assays of HGFIN are performed as treatment is continued.

The methods described herein can, optionally, include the detection of one or more additional indicators of inflammatory disease, such as C-reactive protein. HGFIN and/or an additional indicator of inflammatory disease can be detected, e.g., by an immunoassay, HPLC, or mass spectroscopy.

The invention also provides, in certain embodiments, a method of detecting an indicator of a subject's susceptibility to diseases characterized by systemic inflammation. The method entails assaying a biological sample for HGFIN, wherein the presence of HGFIN at an elevated level indicates the susceptibility to a disease characterized by systemic inflammation.

All of the methods described herein can, but need not, include one or more of the following aspects. HGFIN can be detected in an assay wherein the HGFIN becomes labeled with a detectable label. HGFIN from a sample can transformed from a free state to a bound state by forming a complex with another assay component. HGFIN can be detected in an assay wherein HGFIN initially present in a soluble phase becomes immobilized on a solid phase. HGFIN can be detected in an assay wherein the sample is fractionated to separate HGFIN from at least one other sample component. HGFIN can be detected in an assay wherein HGFIN becomes embedded in a separation medium. HGFIN can be detected in an assay wherein HGFIN is volatilized.

Any of the methods described herein can additionally include recording the HGFIN level, and/or a diagnosis based at least in part on the HGFIN level, in a patient medical record. In specific embodiments, this recordation includes recording the HGFIN level in a computer-readable medium. In variations of such embodiments, the patient medical record is maintained by a laboratory, physician's office, a hospital, a health maintenance organization, an insurance company, and/or a personal medical record website.

All of the methods described herein can, but need not, include one or more of the following aspects. A diagnosis, based at least in part on the HGFIN level, can be recorded on or in a medic alert article selected from a card, worn article, or radiofrequency identification (RFID) tag.

Any of the methods described herein can additionally include one or more of the following: informing the subject of a result of the HGFIN assay and/or of a diagnosis based at least in part on the HGFIN level; prescribing, initiating, and/or altering prophylaxis and/or therapy; and/or ordering and/or performing one or more additional assays. In certain embodiments, the HGFIN level determined in an HGFIN assay is not elevated, and the additional assay comprises an additional HGFIN assay. In other embodiments, the HGFIN level determined in an HGFIN assay is elevated. In variations of embodiments in which HGFIN is determined to be elevated, the additional assay includes an additional HGFIN assay and/or a different assay.

In any of the methods described herein HGFIN can be detected as part of a differential diagnosis.

DETAILED DESCRIPTION

HGFIN is expressed de novo in renal infarcts in rats, in the cortex of remnant rat nephrons after 5/6 nephrectomy, in diabetic rat kidney, in the kidney of patients with Type 1 diabetes who have microalbuminuria and overt proteinuria (but not in the renal cortex of normoalbuminuric diabetic patients or live renal donors), and in the kidney of patients with lupus nephritis in whom there is histological evidence of tubulointerstitial injury, even before serum creatinine rises above the normal range. Immunohistochemistry demonstrates marked expression in interstitial inflammatory cells in the renal infarct after 5/6 nephrectomy, but also in the renal cortical parenchyma, minimally in tubule cells 2 days post-operation, and then more pronounced in tubular cells 2 weeks and 4 weeks post-operation. Tubular cells from pathologically dilated tubules express the most HGFIN, and these are seen regularly sloughing into the urine. These sloughed cells are the likely source of urine HGFIN and are a measure of progressive tubulointerstitial dropout and progressive renal function decline.

Definitions

Terms used in the claims and specification are defined as set forth below unless otherwise specified.

The term "hematopoietic growth factor inducible neurokinin-1 (HGFIN)" refers to a type 1 transmembrane glycoprotein, which has also been referred to as "osteoactivin," "GPNMB," "DC-HIL," See Weterman et al. (1995) Int. J. Cancer 60:73-81; Safadi et al. (2001) J. Cell. Biochem. 84:12-26; Shikano et al. (2001) J. Biol. Chem. 276:8125-34, each of which is incorporated by reference in its entirety.

"Biological samples" that can be assayed using the methods of the present invention include biological fluids, such as kidney tissue and cells, whole blood, blood leukocytes, serum, urine, and urine exosomes.

As used herein with reference to HGFIN, the term "elevated level" refers to a level in a biological sample that is higher than a normal level or range. An "elevated HGFIN level" can be measured based upon HGFIN mRNA, protein, and/or activity. The normal level or range for HGFIN is defined in accordance with standard practice. Thus, the level measured in a particular biological sample will be compared with the level or range of levels determined in similar normal samples. In this context, "normal tissue" is tissue from an individual with no detectable renal disease, renal injury, or systemic inflammatory disease. The level of kidney HGFIN mRNA and protein are said to be "elevated" where the HGFIN is normally undetectable (i.e, the normal level in the kidney cortex is zero), but is detected in a test sample, as well as where the HGFIN is present in the test sample at a higher than normal level or range.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

The term "specific binding" is defined herein as the preferential binding of binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein, the phrase "HGFIN becomes labeled with a detectable label" refers to the binding of a label or labeled moiety to HGFIN, directly or indirectly, via one or more additional moieties.

As used with reference to HGFIN, a "free state" refers to the state of HGFIN before contact with any assay component. This term encompasses HGFIN bound to one or more sample components. The term "bound state" is used to describe HGFIN bound to one or more assay component(s) to form a complex.

The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record may be reviewed by a physician in diagnosing the condition.

As used herein, the term "worn article" refers to any article that can be worn on a subject's body, including, but not limited to, a tag, bracelet, necklace, arm band, or head band.

As used herein, the term "differential diagnosis" refers to the determination of which of two or more diseases with similar symptoms is likely responsible for a subject's symptom(s), based on an analysis of the clinical data.

In General

In certain embodiments, the invention provides methods of detecting hematopoietic growth factor inducible neurokine (HGFIN) as a novel biomarker of renal injury, renal disease, and/or systemic inflammation. These methods entail assaying a biological sample for HGFIN, wherein the level of HGFIN is positively correlated with renal injury, renal disease, and systemic inflammation, respectively.

Sample Collection and Processing

The assay methods of the invention are generally carried out on biological samples derived from an animal, preferably a mammal, and more preferably a human.

The methods of the invention can be carried out using any sample that may contain soluble HGFIN, HGFIN in exosomes, or HGFIN moieties, including its intracellular, transmembrane, or extracellular moieties or any peptide fraction thereof. Convenient samples include, for example, blood, blood cells, serum, plasma, kidney cells, urinary exosomes, and urine.

The sample may be pretreated as necessary by dilution in an appropriate buffer solution or concentrated, if desired. Any of a number of standard aqueous buffer solutions and/or protease inhibitors, employing any of a variety of buffers, such as phosphate, Tris, or the like, at physiological pH, can be used.

Assaying for HGFIN

HGFIN can be detected and quantified by any of a number of methods well known to those of skill in the art for polypeptide detection. These may include analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, dipstick, and the like.

In one embodiment, HGFIN is detected/quantified in an electrophoretic polypeptide separation (e.g. a 1- or 2-dimensional electrophoresis). Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.).

A variation of this embodiment utilizes a Western blot (immunoblot) analysis to detect and quantify the presence of HGFIN in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with antibodies that specifically bind the analyte. Antibodies that specifically bind to the analyte may be directly labeled or alternatively may be detected subsequently using labeled antibodies (e.g., labeled sheep anti-mouse antibodies) that specifically bind to a domain of the primary antibody.

In certain of the above-described embodiments, the sample and/or HGFIN is transformed in some manner in the course of the assay. For example, the sample may be fractionated such that HGFIN is separated from at least one other sample component. The HGFIN can be recovered in a liquid fraction or can be detected while embedded in a separation medium, such as a gel. For mass spectroscopy, HGFIN is volatilized for detection.

In a preferred embodiment, HGFIN is detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

Conventional immunoassays often utilize a "capture agent" to specifically bind to and often immobilize the analyte on a solid phase. In preferred embodiments, the capture agent is an antibody.

Immunoassays also typically utilize a labeled detection agent to specifically bind to and label the binding complex formed by the capture agent and the analyte. The labeled detection agent may itself be one of the moieties making up the antibody/analyte complex. Alternatively, the labeled detection agent may be a third moiety, such as another antibody, that specifically binds to the capture agent/analyte complex. Other polypeptides capable of specifically binding immunoglobulin constant regions, such as polypeptide A or polypeptide G may also make up the labeled detection agent. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542).

Preferred immunoassays for detecting the target polypeptide(s) are either competitive or noncompetitive. Noncompetitive immunoassays are assays in which the amount of captured analyte is directly measured. In competitive assays, the amount of analyte in the sample is measured indirectly by measuring the amount of an added (exogenous) labeled analyte displaced (or competed away) from a capture agent by the analyte present in the sample. In one competitive assay, a known amount of, in this case, labeled HGFIN is added to the sample, and the sample is then contacted with a capture agent. The amount of labeled HGFIN bound to the antibody is inversely proportional to the concentration of HGFIN present in the sample.

Various homogeneous and heterogeneous immunoassay methods are summarized in U.S. Pat. No. 4,279,992 and in IMMUNOASSAYS FOR THE 80s. Voller, A. et al (editors), Baltimore: University Park Press (1981). Enzyme-linked immunosorbent assays (ELISAs) are described by Maggio, et al, ENZYME-IMMUNOASSAY, Boca Raton: CRC Press pp 172-176 (1980) and Tijssen, LABORATORY TECHNIQUES IN BIOCHEMISTRY AND MOLECULAR BIOLOGY: PRACTICE AND THEORY OF IMMUNOASSAYS, vol 15, Elsevier 1985. Well known ELISA formats include: "indirect" ELISA, sandwich ELISA, and competitive ELISA.

In an illustrative embodiment, the steps of "indirect" ELISA include:
1. Apply a sample of known antigen of known concentration to a surface, often the well of a microtiter plate. The antigen is fixed to the surface to render it immobile. Simple adsorption of the protein to the plastic surface is usually sufficient. These samples of known antigen concentrations will constitute a standard curve used to calculate antigen concentrations of unknown samples.
2. A concentrated solution of non-interacting protein, such as bovine serum albumin (BSA) or casein, is added to all plate wells. This step is known as blocking, because these proteins block non-specific adsorption of other proteins to the plate.
3. The plate wells or other surface are then coated with samples of unknown antigen concentration, diluted into the same buffer used for the antigen standards. Since antigen immobilization in this step is due to non-specific adsorption, it is important for the total protein concentration to be similar to that of the antigen standards.
4. The plate is washed, and a detection antibody specific to the antigen of interest is applied to all plate wells. This antibody will only bind to immobilized antigen on the well surface, not to other sample proteins or the blocking proteins.
5. Secondary antibodies, which will bind to any remaining detection antibodies, are added to the wells. These secondary antibodies are conjugated to the substrate-specific enzyme. This step may be skipped if the detection antibody is conjugated to an enzyme.
6. Wash the plate, so that excess unbound enzyme-antibody conjugates are removed.
7. Apply a substrate which is converted by the enzyme to elicit a chromogenic or fluorogenic or electrochemical signal.
8. View/quantify the result using a spectrophotometer, spectrofluorometer, or other optical/electrochemical device. The enzyme acts as an amplifier; even if only few enzyme-linked antibodies remain bound, the enzyme molecules will produce many signal molecules.

Sandwich ELISA can, in specific embodiments, be carried out as follows:
1. Prepare a surface to which a known quantity of capture antibody is bound.
2. Block any non specific binding sites on the surface.
3. Apply the antigen-containing sample to the plate.
4. Wash the plate, so that unbound antigen is removed.
5. Apply primary antibodies that bind specifically to the antigen.
6. Apply enzyme-linked secondary antibodies which are specific to the primary antibodies.
7. Wash the plate, so that the unbound antibody-enzyme conjugates are removed.
8. Apply a substrate which is converted by the enzyme to elicit a chromogenic or fluorogenic or electrochemical signal.
9. View/quantify the result using a spectrophotometer, spectrofluorometer, or other optical/electrochemical device.

A third illustrative ELISA format is based on competitive binding. The steps for this ELISA can include:
1. Unlabeled antibody is incubated in the presence of its antigen.
2. These bound antibody/antigen complexes are then added to an antigen coated well.
3. The plate is washed, so that unbound antibody is removed. (The more antigen in the sample, the less antibody will be able to bind to the antigen in the well, hence "competition.")
4. The secondary antibody, specific to the primary antibody is added. This second antibody is coupled to the enzyme.
5. A substrate is added, and remaining enzymes produce a chromogenic or fluorescent signal.

Some competitive ELISA formats include enzyme-linked antigen rather than enzyme-linked antibody. The labeled antigen competes for primary antibody binding sites with your sample antigen (unlabeled). The more antigen in the sample, the less labeled antigen is retained in the well and the weaker the signal. An ELISA kit for assaying human HGFIN is commercially available from R & D Systems (human Osteoactivin/GPNMB, Product No. DY2550.

The illustrative ELISA formats are described above in terms of a plate as the solid phase on which the assay is carried out. However, as those of skill in the art appreciate, ELISAs can be carried out using a wide variety of solid phases (see this section below), including, e.g., beads.

In an illustrative embodiment, an assay described herein can be carried out in a "dipstick." For example, a dipstick surface can be coated with a capture antibody for HGFIN, and an enzyme-labeled detection antibody against a different epitope of HGFIN can be used to detect HGFIN that binds to the capture antibody. Examples of methods and kits that can be adapted to the present invention include those described in U.S. Pat. No. 5,656,503, issued to May et al. on Aug. 12, 1997, U.S. Pat. No. 6,500,627, issued to O'Conner et al. on Dec. 31, 2002, U.S. Pat. No. 4,870,007, issued to Smith-Lewis on Sep. 26, 1989, and U.S. Pat. No. 4,632,901, issued to Valkers et al. on Dec. 30, 1986, all such references being hereby incorporated by reference in their entireties for their teachings regarding assay methods and kits.

The assays of this invention are scored (as positive or negative or quantity of analyte) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of analyte concentration. ELISA may be run in a qualitative or quantitative format. Qualitative results provide a simple positive or negative result for a sample. The cutoff between positive and negative is determined by the analyst and may be statistical. Two or three times the standard deviation is often used to distinguish positive and negative samples. In quantitative ELISA, the optical density or fluorescent units of the sample is interpolated into a standard curve, which is typically a serial dilution of the target.

Antibodies

Antibodies useful in the immunoassay methods of the invention include polyclonal and monoclonal antibodies. Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience.

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naïve" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley antibody laboratories, Bethyl Laboratories, Anawa, Eurogenetec, etc.).

Solid Phase

For embodiments of the invention that employ a solid phase as a support for the capture agent, the solid phase can be any suitable porous material with sufficient porosity to allow access by reagents and a suitable surface affinity to bind a capture agent. Microporous structures are generally preferred, but materials with gel structure in the hydrated state may be used as well. Useful solid supports include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials);

and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto, bonded, or laminated to appropriate inert carriers, such as paper, glass, plastic films, fabrics, or the like.

The porous structure of nitrocellulose has excellent absorption and adsorption qualities for a wide variety of reagents including monoclonal antibodies. Nylon also possesses similar characteristics and also is suitable.

Porous solid phases useful in the invention can be in the form of sheets of thickness from about 0.01 to 0.5 mm, e.g., about 0.1 mm. The pore size may vary within wide limits, and is preferably from about 0.025 to about 15 microns, especially from about 0.15 to about 15 microns.

Preferred solid phase materials for flow-through assay devices include filter paper such as a porous fiberglass material or other fiber matrix materials. The thickness of such material is not critical and will be a matter of choice, largely based upon the properties of the sample or analyte being assayed, such as the fluidity of the biological sample.

Alternatively, the solid phase can constitute microparticles. Microparticles useful in the invention can be selected by one skilled in the art from any suitable type of particulate material and include those composed of polystyrene, polymethylacrylate, polypropylene, latex, polytetrafluoroethylene, polyacrylonitrile, polycarbonate, or similar materials.

Microparticles can be suspended in the mixture of soluble reagents and biological sample or can be retained and immobilized by a support material. In the latter case, the microparticles on or in the support material are not capable of substantial movement to positions elsewhere within the support material.

The methods of the present invention can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture agent(s) can be affixed, directly or indirectly, to the electrode(s). In one embodiment, for example, capture agents can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture agent can be attached to the solid phase by adsorption on the porous material, where it is retained by hydrophobic forces. Alternatively, the surface of the solid phase can be activated by chemical processes that cause covalent linkage of the capture agent to the support.

To change or enhance the intrinsic charge of the solid phase, a charged substance can be coated directly onto the solid phase material or onto microparticles which then are retained by a solid phase material. Ion capture procedures for immobilizing an immobilizable reaction complex with a negatively charged polymer, described in U.S. application Ser. No. 150,278, corresponding to EP Publication No. 0326100, and U.S. application Ser. No. 375,029 (EP Publication No. 0406473), can be employed according to the present invention to affect a fast solution-phase immunochemical reaction. In these procedures, an immobilizable immune complex is separated from the rest of the reaction mixture by ionic interactions between the negatively charged polyanion/immune complex and the previously treated, positively charged porous matrix and detected by using any of a number of signal-generating systems, including, e.g., chemiluminescent systems, as described in U.S. application Ser. No. 921,979, corresponding to EPO Publication No. 0 273, 115.

If the solid phase is silicon or glass, the surface must generally be activated prior to attaching the specific binding partner. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio] propionate), SMCC (succinimidyl-4-[Nmaleimidomethyl] cyclohexane-1-carboxylate), SIAB (succinimidyl [4iodoacetyl] aminobenzoate), and SMPB (succinimidyl 4-[1maleimidophenyl] butyrate) to separate the capture agent from the surface. Vinyl groups can be oxidized to provide a means for covalent attachment. Vinyl groups can also be used as an anchor for the polymerization of various polymers such as poly-acrylic acid, which can provide multiple attachment points for specific capture agents. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture agent on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize non-specific binding of labeled entities and compatability with the labeling system employed. For, example, solid phases used with fluorescent labels should have sufficiently low background fluorescence to allow signal detection.

Following attachment of a specific capture agent, the surface of the solid support may be further treated with materials such as serum, proteins, or other blocking agents to minimize non-specific binding.

Labeling Systems

As discussed above, many immunoassays according to the invention employ a labeled detection agent.

Detectable labels suitable for use in the detection agents of the present invention include any composition detectable by spectroscopic, photochemical, biochemical, immunochemical, electrical, optical, or chemical means. Useful labels in the present invention include magnetic beads (e.g., Dynabeads™), fluorescent dyes (e.g., fluorescein, texas red, rhodamine, green fluorescent protein, and the like, see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^{3}$H, $^{125}$I, $^{35}$S, $^{14}$C, $^{32}$P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection agent prior to, or during, or after contact with the biological sample. So-called "direct labels" are detectable labels that are directly attached to or incorporated into detection agents prior to use in the assay. Direct labels can be attached to or incorporated into detection agents by any of a number of means well known to those of skill in the art.

In contrast, so-called "indirect labels" typically bind to the detection agent at some point during the assay. Often, the indirect label binds to a moiety that is attached to or incorporated into the detection agent prior to use. Thus, for example, an antibody used as a detection agent (a "detection antibody") can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. Such polypeptides can thus be labeled and added to the assay mixture, where they will bind to the detection antibody.

Some labels useful in the invention may require the use of an indicator reagent to produce a detectable signal. In an ELISA, for example, an enzyme label (e.g., beta-galactosidase) will require the addition of a substrate (e.g., X-gal) to produce a detectable signal.

HGFIN Levels

It may be advantageous, in some embodiments, to normalize the value obtained upon measuring HGFIN in an assay using some other parameter of the biological sample. For example, the concentration of urine components will vary, depending upon how concentrated or dilute the urine sample is. Accordingly, to obtain a meaningful HGFIN level, it is typically desirable to normalize the measured HGFIN value using another parameter of urine that varies with the degree of concentration of the urine. Thus, for example, HGFIN can be normalized by dividing the measured concentration of HGFIN in urine (e.g., in picograms/dl) by the concentration of a urinary protein, such as creatinine (e.g., in milligrams/dl). As used herein, the term "HGFIN level" includes the concentration measured in the assay, as well as any normalized level that could be calculated, based on one or more other sample parameters.

Once determined, an HGFIN level can be recorded in a patient medical record. In certain embodiments, the methods of the invention include making a diagnosis, often a differential diagnosis, based at least in part on the HGFIN level. This diagnosis can also be recorded in a patient medical record. For example, in various embodiments, the diagnosis of renal injury, renal disease (acute or chronic), and/or an inflammatory disease (e.g., a systemic inflammatory disease) is recorded in a medical record. The medical record can be in paper form and/or can be maintained in a computer-readable medium. The medical record can be maintained by a laboratory, physician's office, a hospital, a health maintenance organization, an insurance company, and/or a personal medical record website. In certain embodiments, a diagnosis, based at least in part on the HGFIN level, is recorded on or in a medic alert article such as a card, a worn article, and/or a radiofrequency identification (RFID) tag.

In particular embodiments, the methods of the invention include informing the subject of a result of the HGFIN assay and/or of a diagnosis based at least in part on the HGFIN level. The patient can be informed verbally, in writing, and/or electronically.

The methods of the invention can include prescribing, initiating, and/or altering prophylaxis and/or therapy, e.g., for renal injury, renal disease (acute or chronic), and/or an inflammatory disease (e.g., a systemic inflammatory disease). In certain embodiments, the methods can entail ordering and/or performing one or more additional assays. For example, if the HGFIN level is determined to be within a normal range (i.e., not elevated), the HGFIN assay may be repeated to rule out a false negative result, and/or one or more additional HGFIN assays may be performed to monitor the subject's status. If the HGFIN level is determined to be elevated, it may be desirable to repeat the HGFIN assay to rule out a false positive result. In certain embodiments, it will be desirable to assay another indicator of, e.g., renal injury, renal disease (acute or chronic), and/or an inflammatory disease (e.g., a systemic inflammatory disease), to confirm a diagnosis. Examples of other indicators of renal injury or disease include serum creatinine, serum cystatin-C, urine protein, urine albumin, urine N-acetyl-beta-D-glucosaminidase, urine NGAL, and urine KIM-1. C-reactive protein is an example of an indicator of systemic inflammatory disease. Urine HGFIN may be sequentially measured in patients in whom the assay shows kidney injury in order to demonstrate remission or the propensity to achieve a remission, and in those with remission, in order to predict relapse of kidney injury before it is otherwise clinically apparent. In the setting of experimental drug testing, urine HGFIN may be used alone or as a member of a biomarker panel to demonstrate early kidney injury either in preclinical and/or clinical testing.

Test Kits

The invention also provides a test kit for assaying for HGFIN. Test kits according to the invention include one or more reagents useful for practicing one or more immunoassays according to the invention. A test kit generally includes a package with one or more containers holding the reagents, as one or more separate compositions or, optionally, as admixture where the compatibility of the reagents will allow. The test kit can also include other material(s) that may be desirable from a user standpoint, such as a buffer(s), a diluent(s), a standard(s), and/or any other material useful in sample processing, washing, or conducting any other step of the assay.

Test kits according to the invention preferably include instructions for carrying out one or more of the immunoassays of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

EXAMPLES

The following examples are offered to illustrate, but not to limit, the claimed invention.

Example 1

HGFIN is a Marker of Injury in Diverse Renal Disease Across Species

Body: HGFIN is a type 1 transmembrane glycoprotein and negative regulator of inflammation in macrophages also present in osteoclasts, melanoma and dendritic cells, skeletal muscle, retinal pigment epithelium, and renal tubules. A truncating mutation is associated with diabetic nephropathy (DN) sensitivity in mice. Upregulation inhibits experimental cirrhosis. We tested whether HGFIN dysregulation occurs in diverse renal injury across species. We performed 5/6nephrectomy (Nx) in rats and microarrays with Affymetrix chip 230_2 on renal cortex at 2 days, 2 weeks, and 4 weeks post-op, using initial Nx as control. HGFIN array result was validated by real-time and semiquantitative (sq) PCR. For generalizability, renal cortical HGFIN PCR was also performed in: 1) SZ rats with diabetes mellitus (DM)×4 mos and controls; and 2) Insulin-dependent diabetes mellitus (IDDM) patients with normoalbuminuria (NA), microalbuminuria (MA), overt diabetic nephropathy (DN) and live renal donors (LRD). Urine HGFIN/creatinine was measured by immunoblotting in 5/6Nx and Nx and immunohistochemistry (IH) localized renal HGFIN.

Results: Array HGFIN was confirmed in 5/6Nx by real-time PCR: 50-fold at day 2 ($p<0.001$), 48-fold at week 2 ($p<0.001$), and 42-fold at week 4 ($p<0.001$) and confirmed by sq PCR, but at lower magnitude. HGFIN mRNA (real-time) was also increased in SZ-DM rats versus controls (11-fold, $p<0.01$). In IDDM, renal cortical HGFIN mRNA in NA was similar to LRD ($p>0.05$), but was increased in MA (4.6-fold) and overt DN (4.7-fold) compared to NA and LRD ($p<0.05$). By IH HGFIN was rarely observed in Nx. In 5/6Nx, HGFIN was identified in the cytoplasm of some dilated and fewer non-dilated proximal tubules in a punctate, globular pattern and similarly, seen focally in glomeruli in scattered reactive parietal epithelial cells and few hypertrophic podocytes. Urine HGFIN/creatinine was higher in 5/6Nx versus control ($p=0.014$). These data show increased renal cortical HGFIN in rats and humans in diverse injury; renal epithelial localization; and increased urine excretion. Using ELISA methodology, we have preliminarily identified a normal range for human urine HGFIN as <90 pg/mg creatinine in 20 healthy adults without known renal disease. Confirmation/replications of this study can readily be carried out in additional normal subjects. HGFIN may function biologically beyond its role as a biomarker and promote an adaptive response in evolving chronic kidney disease by facilitating cell survival by enhancing autophagy.

Example 2

Upregulation of Monocyte/Macrophage HGFIN in End-Stage Renal Disease

HGFIN is a type 1 transmembrane glycoprotein which is expressed in numerous cell types including osteoclasts, myocytes, retinal pigment epithelium, renal tubules, macrophages, and dendritic cells. It serves as an osteoblast differentiation factor, participates in bone mineralization, and functions as a negative regulator of inflammation in macrophages. Monocyte transformation to tissue macrophages triggers HGFIN expression. CKD is associated with systemic inflammation, arteriosclerosis, bone demineralization, and soft tissue-vascular calcification/ossification. Since HGFIN is involved in inflammation and mineralization, processes which are affected by CKD, we explored its expression in circulating monocytes and monocyte-derived macrophages in a group of 14 hemodialysis-dependent patients and 10 age-matched controls. HGFIN, colony stimulating factor (CSF), IL-6, TNFa, IL-I0 and beta-actin mRNA abundance were measured by real time PCR in isolated blood monocytes before and seven days after in vitro transformation to macrophages. Dialysis patients exhibited marked upregulation of CSF and IL-6 and significant downregulation of IL10 in both intact and transformed monocytes. HGFIN expression in intact monocytes was negligible in controls but conspicuously elevated (8.6-fold) in dialysis patients. As expected, in vitro monocyte-to-macrophage transformation resulted in marked upregulation of HGFIN in cells obtained from both groups but much more so in dialysis patients (17.5-fold higher). Thus, intact monocytes from dialysis patients exhibit early features of macrophage transformation while still in the circulation (as evidenced by heightened CSF and HGFIN expressions) and an exaggerated response upon transformation. Further studies have been carried to determine the role of heightened monocyte/macrophage HGFIN expression in the pathogenesis of CKD-induced vascular-soft tissue calcification and inflammation. (Published in Oct. 15, 2009 CJASN issue, doi: 10.2215/CJN.03390509), which is hereby incorporated by reference in its entirety.

Example 3

Measurement of HGFIN in Human Urine Samples

An ELISA for assaying human HGFIN from R & D Systems (human Osteoactivin/GPNMB, Product No. DY2550 was used to assay urine samples from 20 normal human subjects (i.e., who did not have any evidence of kidney disease/injury). Under the conditions of this assay, normal HGFIN concentrations (normalized to creatinine) were less than about 90 pg/mg creatinine.

What is claimed is:

1. A method of detecting an indicator of renal injury or renal disease in a subject, the method comprising assaying a urine sample from the subject for hematopoietic growth factor inducible neurokinin-1 (HGFIN), wherein the presence of HGFIN at an elevated level in comparison to a normal level from an individual with no detectable renal disease or renal injury indicates the presence and/or degree of renal injury or renal disease, and/or the rate of loss of kidney function, wherein the assayed HGFIN is soluble HGFIN and/or HGFIN in exosomes.

2. The method of claim 1, wherein the urine sample comprises a human urine sample.

3. A method of detecting an indicator of renal injury or renal disease in a subject, the method comprising assaying a urine sample from the subject for hematopoietic growth factor inducible neurokinin-1 (HGFIN), wherein the urine sample comprises centrifuged urine, wherein the presence of HGFIN at an elevated level in comparison to a normal level from an individual with no detectable renal disease or renal injury indicates the presence and/or degree of renal injury or renal disease, and/or the rate of loss of kidney function.

4. The method of claim 3, wherein the urine sample comprises urinary exosomes.

5. The method of claim 2, wherein the human is a human patient known to have, or suspected of having, renal injury or renal disease.

6. The method of claim 5, wherein the human patient is known to have, or suspected of having, renal injury.

7. The method of claim 5, wherein the human patient is known to have, or suspected of having, acute renal disease.

8. The method of claim 5, wherein the human patient is known to have, or suspected of having, chronic renal disease.

9. A method of detecting an indicator of a subject's response to treatment for renal injury or renal disease, the method comprising assaying a urine sample obtained from the subject after initiation of treatment for renal injury or renal disease for hematopoietic growth factor inducible neurokinin-1 (HGFIN), wherein an elevated level of HGFIN in comparison to a normal level from an individual with no detectable renal disease or renal injury is positively correlated with the degree of renal injury or renal disease or the rate of loss of renal function, wherein the assayed HGFIN is soluble HGFIN and/or HGFIN in exosomes.

10. The method of claim 1, additionally comprising detecting one or more additional indicators of renal injury or disease selected from the group consisting of serum creatinine, serum cystatin-C, urine protein, urine albumin, urine N-acetyl-beta-D-glucosaminidase, urine NGAL, and urine KIM1.

11. The method of claim 1, wherein HGFIN is detected by a method selected from the group consisting of an immunoassay, HPLC, and mass spectroscopy.

12. The method of claim 1, wherein HGFIN is detected in an assay wherein the HGFIN becomes labeled with a detectable label.

13. The method of claim 1, wherein HGFIN is detected in an assay wherein the HGFIN is transformed from a free state to a bound state by forming a complex with another assay component.

14. The method of claim 1, wherein HGFIN is detected in an assay wherein HGFIN initially present in a soluble phase becomes immobilized on a solid phase.

15. The method of claim 1, wherein HGFIN is detected in an assay wherein the sample is fractionated to separate HGFIN from at least one other sample component.

16. The method of claim 1, wherein HGFIN is detected in an assay wherein HGFIN becomes embedded in a separation medium.

17. The method of claim 1, wherein HGFIN is detected in an assay wherein HGFIN is volatilized.

18. The method of claim 1, additionally comprising recording the HGFIN level, and/or a diagnosis based at least in part on the HGFIN level, in a patient medical record.

19. The method of claim 18, wherein said recording comprises recording the HGFIN level in a computer-readable medium.

20. The method of claim 18, wherein said patient medical record is maintained by a laboratory, physician's office, a hospital, a health maintenance organization, an insurance company, or a personal medical record website.

21. The method of claim 1, wherein a diagnosis, based at least in part on the HGFIN level, is recorded on or in a medic alert article selected from a card, worn article, or radiofrequency identification (RFID) tag.

22. The method of claim 1, additionally comprising informing the subject of a result of the HGFIN assay and/or of a diagnosis based at least in part on the HGFIN level.

23. The method of claim 1 additionally comprising prescribing, initiating, and/or altering prophylaxis and/or therapy.

24. The method of claim 1, additionally comprising ordering and/or performing one or more additional assays.

25. The method of claim 24, wherein the HGFIN level determined in said assay is not elevated, and the additional assay comprises an additional HGFIN assay.

26. The method of claim 24, wherein the HGFIN level determined in said assay is elevated.

27. The method of claim 26, wherein the additional assay comprises an additional HGFIN assay.

28. The method of claim 26, wherein the additional assay comprises a different assay.

29. The method of claim 1, wherein HGFIN is detected as part of a differential diagnosis.

\* \* \* \* \*